United States Patent [19]

MacAnally

[11] 4,148,550
[45] Apr. 10, 1979

[54] ROD LENS ASSEMBLY AND METHOD OF MAKING THE SAME

[75] Inventor: Richard B. MacAnally, Altadena, Calif.

[73] Assignee: American Hospital Supply Corporation, Evanston, Ill.

[21] Appl. No.: 795,404

[22] Filed: May 9, 1977

[51] Int. Cl.² .............................................. G02B 23/16
[52] U.S. Cl. ........................................ 350/54; 350/70; 350/178; 350/242; 350/320
[58] Field of Search ........................ 350/54, 69, 70, 80, 350/178, 242, 252, 320

[56] References Cited

U.S. PATENT DOCUMENTS

| | | | |
|---|---|---|---|
| 2,453,862 | 11/1948 | Salisbury | 350/70 X |
| 3,133,143 | 5/1964 | Strang et al. | 350/54 X |
| 4,036,218 | 7/1977 | Yamashita et al. | 350/252 X |
| 4,063,796 | 12/1977 | Hiltebrandt | 350/70 |

Primary Examiner—John K. Corbin
Assistant Examiner—Matthew W. Koren
Attorney, Agent, or Firm—Tilton, Fallon, Lungmus & Chestnut

[57] ABSTRACT

A rod lens assembly for endoscopes and the like which includes an inner tube or barrel disposed in spaced or floating relation within a protective outer tube, the outer tube preferably including an inner layer of light-transmitting fibers and the inner tube containing a plurality of axially-spaced image-transmitting rod lenses. The wall portions of the barrel extending between the ends of adjacent lenses are provided with openings to allow precise positioning of the lenses during assembly and to provide zones of preferential flexure of the barrel when the entire assembly is flexed in normal use. In one embodiment, the cylindrical lenses are fixed in place by clamping forces exerted by the normally non-cylindrical walls of the barrel. The method for making such an assembly, including the steps of inserting, adjusting, securing, and cleaning the lenses, is also disclosed.

21 Claims, 10 Drawing Figures

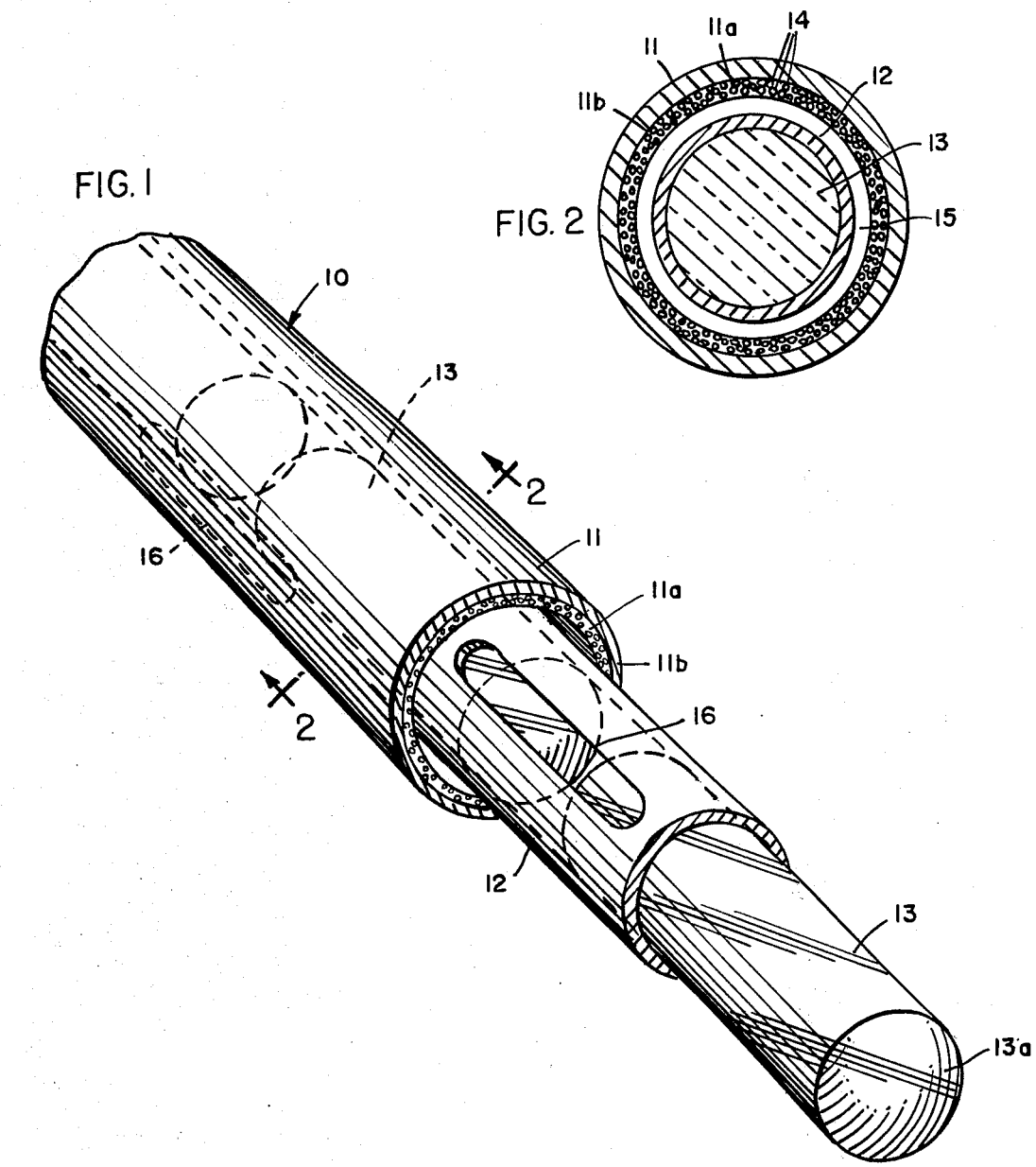
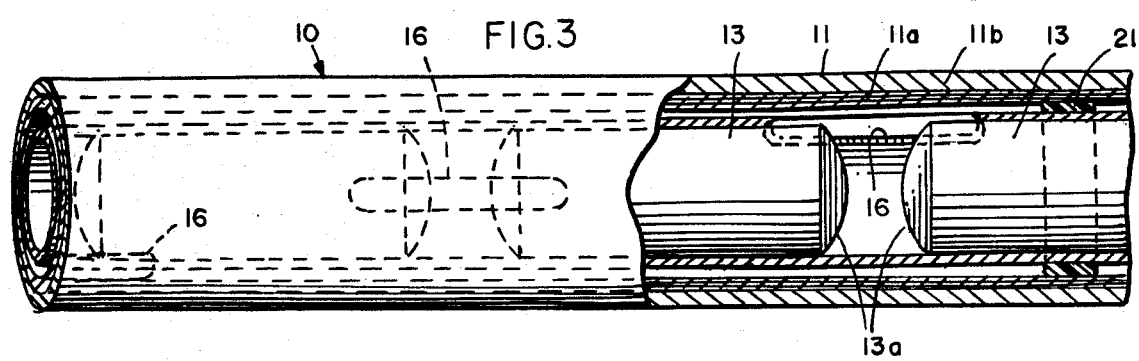

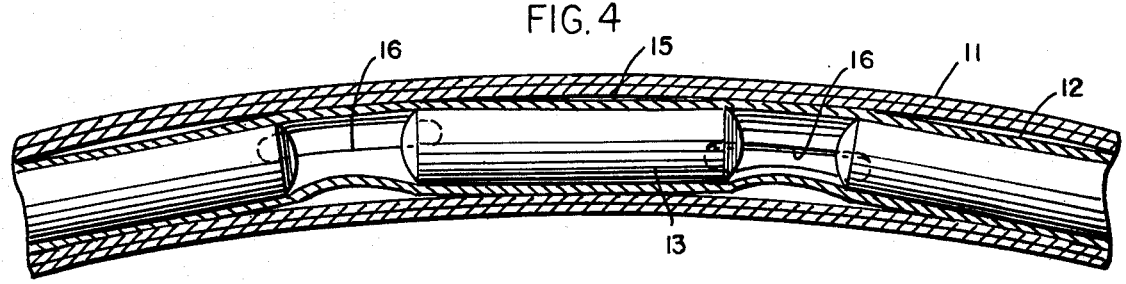
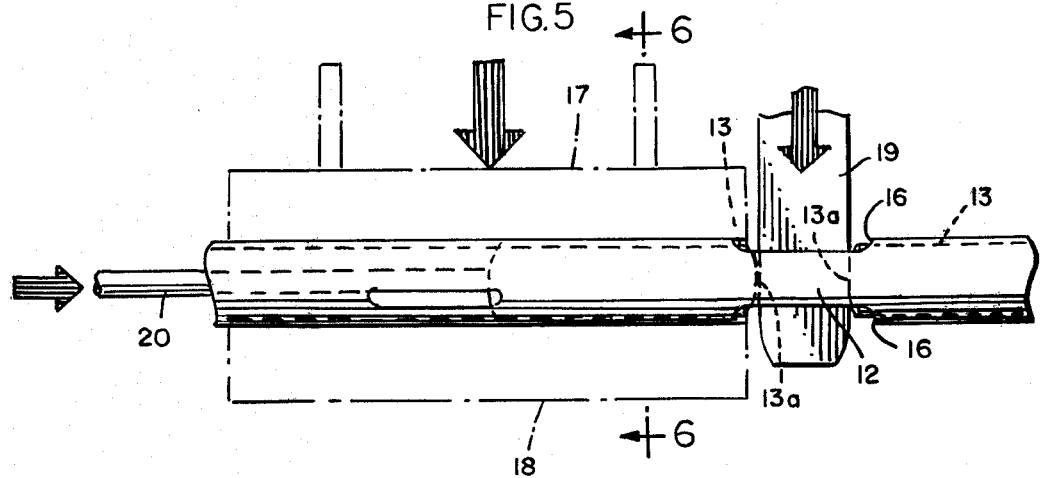
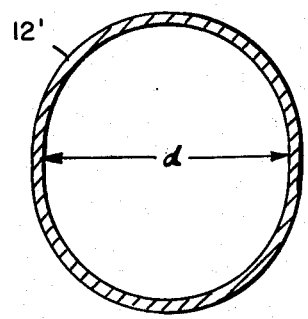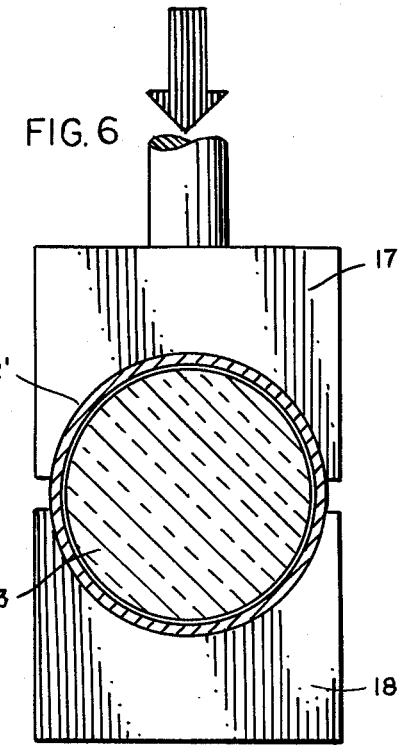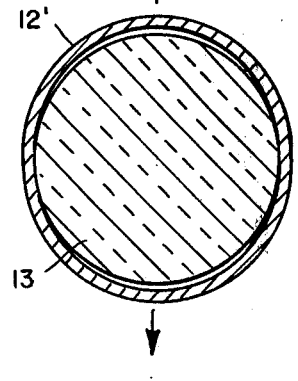

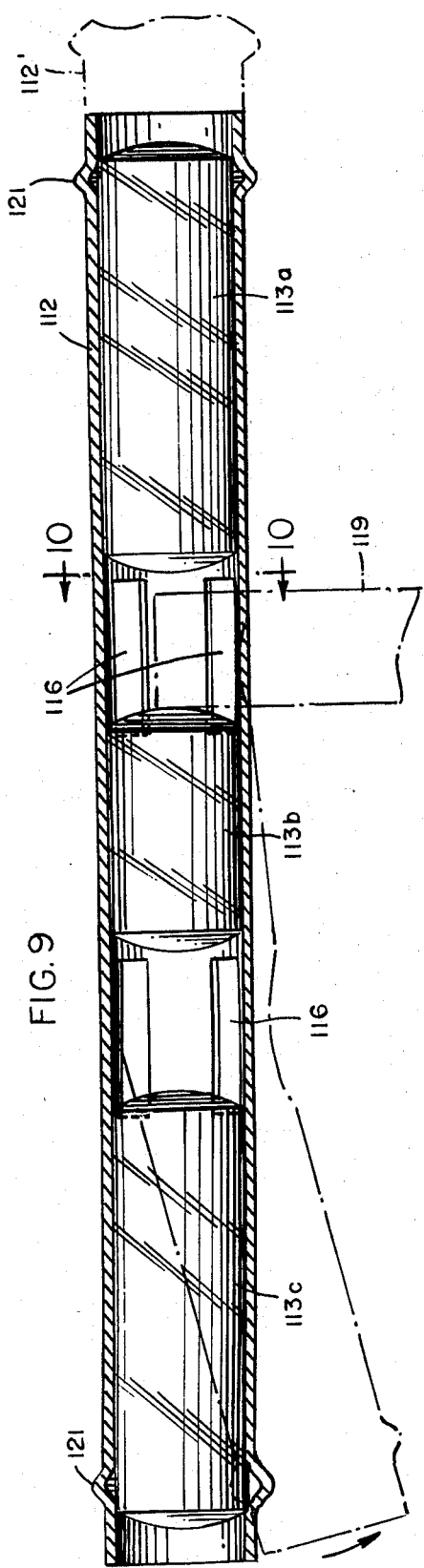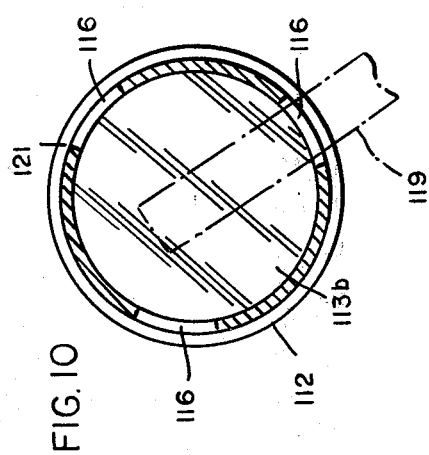

ROD LENS ASSEMBLY AND METHOD OF MAKING THE SAME

BACKGROUND

A conventional rod lens assembly comprises a small-bore flexible tube containing a series of cylindrical rod lenses maintained in axially-spaced relation by small cylindrical sleeves or spacers positioned between the lenses, as illustrated, for example, in U.S. Pat. No. 3,257,902. Even where the wall thickness of the spacers is kept to a minimum and care is taken to insure that the annular ends of those spacers contact the lenses only at their outer edges, such spacers nevertheless significantly reduce the light and image transmitting properties of the lenses by rendering portions of their end faces optically inoperative. In addition, flexure of such an assembly in use may cause the spacing sleeves to abrade or damage the edges and end faces of the lenses, not only resulting in the creation of objectionable debris but also causing possible changes in the critical distances between adjacent lenses. While the risk of damage to the lenses might be reduced by increasing the wall thickness of the spacers, so that they engage larger portions of the end surfaces of the lenses, such a modification is otherwise self-defeating because of further unacceptable reductions in light and image transmission.

An even more serious problem inherent in the construction of a typical rod lens system as so described is the possibility that flexure of the assembly may result in transverse fracture of one or more of the glass lenses, thereby rendering the entire system inoperative and requiring either costly and time-consuming repair or total replacement of the entire assembly. The seriousness of the problem is compounded by the fact that an endoscope containing such a rod lens system is commonly used in conjunction with working elements, deflecting bridges, grasping forceps, lithotrites, and other relatively heavy surgical or urological instruments which, if brought into forceful accidental engagement with the lens-containing tube of such an endoscope, might easily cause flexure of the tube and fracture one or more of the lenses.

The use of spacers to set the spacing between successive rod lenses of a series during assembly thereof has the further disadvantage that even a slight variation from the optimum length of each sleeve could result in a tolerance buildup which might substantially impair the optical properties of the final product. Conversely, the almost-microscopic adjustments in the axial positioning of the lenses which might be needed to provide the best optical performance for the lens train as a whole would be extremely difficult if not virtually impossible to achieve in a system where sleeves must be inserted to set the spacing between successive lenses of the series.

SUMMARY

This invention is concerned with a rod lens assembly, and its method of construction, which overcome the aforementioned disadvantages and other shortcomings of the prior art. Specifically, the improved assembly is characterized by exceptional durability, the attainment of an extremely high level of precision in the spacing of the lens elements, the maintenance of such critical spacing despite repeated flexure of the assembly in normal use, the elimination of spacer sleeves and the optically obstructing effects thereof, and the substantial elimination of optical interferences resulting from particulate matter entrapped or generated within the system.

In brief, the assembly makes use of at least one rod lens cartridge consisting essentially of a plurality of rod lenses mounted in axially-spaced relation in an inner tube or barrel. In those areas where such spacing occurs, the wall of the barrel is provided with axially-elongated slots or openings. Such slots serve as entry ports for a spacing tool or jig which contacts one or both of the opposing end faces of each pair of lenses to control the relative positioning of those lenses during the assembly process. In addition, the slots or openings permit the circulation of fluids (gases or liquids) for the purpose of cleaning or otherwise treating all of the accessible surfaces of the barrel and rod lenses, especially those surfaces in the inter-lens spaces, following the mounting of the rod lenses within the barrel. After the thoroughly cleaned cartridge has been sealed within a protective outer tube, the slots continue to play an important role in helping to define preferential zones of flexure for the inner tube or barrel, thereby reducing strain on the fragile rod lenses, and the possibilities of breakage of those lenses, when the complete assembly is flexed or bent in normal use. Immediate installation of the cartridge in the tube of an instrument is not necessary, however, the cartridge may instead be sealed in a suitable container and stored for future delivery and/or installation as a replacement unit.

The preferential flexure of the wall portions of the barrel extending between the opposing faces of adjacent rod lenses is facilitated by an annular space between the cartridge and the outer tube. In effect, a floating relationship exists between the inner and outer tubes, notwithstanding annular support elements which may be located at selected longitudinally-spaced positions along the tubes to limit unnecessary movement between the parts and, where more than one cartridge is utilized, to insure proper axial alignment of the cartridges or modules within the outer tube. Because of the floating relationship, the cartridge automatically adjusts its position within the outer tube as the entire assembly is flexed so that the outer tube may assume a smoothly curved condition while the inner tube flexes only along those wall portions extending between adjacent rod lenses of the series. The transmission of tensioning forces which might otherwise break the small-diameter rod lenses is thereby avoided or greatly reduced.

While only a single slot need be provided in the wall of the inner tube in register with the space between each pair of lenses, at least a pair of such slots is preferred at each such location, especially if the slots are to be used for the circulation of a cleansing fluid as well as for the entry and withdrawal of a spacing tool. A plurality of such slots at each location is also considered desirable in promoting preferential flexure of the cartridge in the wall areas extending between (rather than about) the rod lenses. Progressive circumferential staggering of the slots from one inter-lens location to the next is also believed desirable in achieving proper flexing characteristics of the assembly as a whole.

While various means may be used to secure the rod lenses within the inner tube or barrel, a clamping arrangement, utilizing a barrel of slightly non-circular (e.g., slightly oval or triangular) sectional configuration, is believed particularly effective. In a normal untensioned state, the barrel has an inside diameter along a minor transverse axis which is less than the diameter of the cylindrical rod lenses; however, when the barrel is squeezed into a generally cylindrical shape, its inside dimensions are great enough to permit longitudinal movement of the lenses into their selected positions of adjustment. Therefore, during an assembly procedure, the barrel is flexed into cylindrical configuration, the lenses are inserted into the barrel and are precisely positioned by means of one or more spacing tools inserted through the slotted wall of the barrel and engaging the end faces of the lenses, and the deforming forces are then withdrawn to permit the barrel to return into an oval configuration to clamp the lenses in their operative positions.

Other features, advantages, and objects of the invention will become apparent from the specification and drawings.

DRAWINGS

FIG. 1 is a fragmentary perspective view of an ensheathed rod lens assembly embodying the present invention.

FIG. 2 is an enlarged cross sectional view taken along line 2—2 of FIG. 1.

FIG. 3 is an elevational view, taken partly in longitudinal section, of the rod lens assembly shown in FIGS. 1 and 2.

FIG. 4 is a longitudinal sectional view of a completed rod lens assembly showing the relationship of parts when the assembly is flexed, the deformation and spacing being depicted in somewhat exaggerated form for illustration purposes.

FIG. 5 is a side elevational view illustrating the steps of inserting and adjusting rod lenses within a supporting barrel, a pair of deforming jaws or shoes being illustrated in broken lines to depict a modification of the method in which a barrel of non-circular cross section (when untensioned) is used.

FIG. 6 is an enlarged cross sectional view taken along line 6—6 of FIG. 5 but showing the clamping members in solid lines.

FIG. 7 is a cross sectional view of the tubular barrel in its normal untensioned state.

FIG. 8 is a cross sectional view showing the barrel with a cylindrical rod lens secured therein.

FIG. 9 is a longitudinal sectional view of a rod lens assembly constituting a second embodiment of the invention.

FIG. 10 is an enlarged cross sectional view taken along line 9—9 of FIG. 9.

DESCRIPTION

Referring to the drawings, the numeral 10 generally designates a rod lens assembly comprising an outer tube 11, an inner tube or barrel 12, and a series of rod lenses 13. The rod lenses are formed of high quality optical glass and have end faces 13a which are ground, polished, and positioned for image transmission. It is to be understood that each of the cylindrical rod lenses 13 may be a composite of several lens elements, all as well known in the art. Since the construction, end-face configuration, and composition of such rod lenses do not constitute a part of this invention, except to the extent that such lenses are generally cylindrical in shape and are capable of being arranged to transmit an optical image, further discussion of those factors is believed unnecessary herein.

As shown most clearly in FIGS. 1 and 2, outer tube 11 is preferably formed in two layers. An inner layer 11a is composed of light-transmitting glass fibers 14 embedded in a suitable matrix formed of epoxy resin or other plastic material. The fibers extend continuously from one end of the assembly to the other and are adapted to transmit light through that assembly to illuminate a body cavity or passage. The outer layer 11b takes the form of a protective sheath or shell. While any suitable material might be used for the sheath, a strong durable metal such as stainless steel has been found particularly effective.

The inner tube or barrel 12 has an outside diameter which is substantially less than the internal diameter of outer tube 11. The annular space 15 between the external surface of the inner tube and the internal surface of the outer tube has a width or radial dimension which is approximately 20 to 40 percent of the combined width of space 15 and sheath 11b. Such a relationship is important in achieving a final assembly in which maximum flexure (i.e., to the point of wall rupture or fracture) of the metal sheath will occur before any appreciable bending forces are exerted upon the rod lenses mounted within the barrel. A preferred range has been calculated to be about 25 to 35 percent. Such relationships take into consideration that the maximum outside diameter of a rod lens assembly intended for use in an adult urological endoscope, that is, the outside diameter of tube 11, should not exceed approximately 0.160 inches, and that a reasonable minimum diameter for rod lenses 13 intended for such use is approximately 0.100 inches. By way of illustrative example, in an assembly utilizing rod lenses of 0.100 outside diameter and a sheath 11b of 0.159 external diameter, the light-transmitting layer 11a may have a thickness of approximately 0.010 inches, the metal sheath's wall thickness may be about 0.010 inches, the inner tube's wall thickness may be approximately 0.005 inches, and the annular space 15 may have a radial width of approximately 0.0045 inches.

Like sheath 11b, the inner tube or barrel 12 may be formed of a metal such as stainless steel, although other materials might conceivably be used. Slots or openings 16 are provided in the wall of the inner tube, each slot extending longitudinally in opposite directions beyond the end face of at least one rod lens and, in the best mode presently known for practicing the invention, extending in opposite axial directions beyond the opposing end faces of a pair of such lenses. Thus, in the preferred embodiment, each slot bridges the space between the opposing ends of a pair of adjacent rod lenses 13 mounted within the tube. Preferably, a plurality of slots 16 are provided at each such location; in the embodiment of FIGS. 1-5, a pair of slots are arranged in diametric opposition at each such location although a triad of slots may be provided and may even be preferred. Also, as illustrated in FIGS. 1, 3 and 4, the slots between successive lenses of the series are staggered at any angular distance (preferably uniform) which is less than 180°. In the embodiment illustrated, such slots are staggered or offset at angular increments of 60°; however, a greater or smaller increment may be used.

The rod lenses may be secured within the inner tube or barrel 12 by any suitable means. A wide variety of adhesives and cements are known which are capable of adhering to the different materials of the barrel and lenses. If desired, a thermosetting or ultraviolet light-activated adhesive might be used, the barrel being heated or exposed to light following accurate positioning of the lenses to set the adhesive and anchor the lenses in place.

FIGS. 6–8 reveal that the lenses may be secured in place within the barrel by means of a clamping or gripping action exerted by diametrically opposing portions of the barrel wall. Referring to FIG. 7, it will be noted that barrel 12' has a non-circular (oval) cross sectional configuration. The inside diameter d along the minor axis when the barrel is in an untensioned state is less than the outside diameter of rod lens 13; however, when the barrel is pressed or squeezed into a generally cylindrical configuration, its internal diameter is slightly greater than the diameter of the lens (FIG. 6). Consequently, in an assembly operation, the barrel 12' may be squeezed between clamping members or shoes 17 and 18 until it assumes a generally cylindrical configuration. After the rod lenses are slid into position and adjusted so that their end faces are spaced precise predetermined distances apart, the distorting forces exerted by shoes 17 and 18 are withdrawn and the wall of the barrel returns to an oval cross sectional configuration with opposing wall portions aligned with the minor transverse axis bearing tightly against the rod lenses to hold the optical elements in position (FIG. 8).

While the above operation has been described in connection with the use of an oval barrel, it will be understood that other non-circular variations might be employed. Thus, similar results might be achieved utilizing a barrel which in its normal untensioned state departs from a true circular configuration by being slightly triangular in shape. Forces exerted against the apexes would therefore cause the barrel to assume a cylindrical cross section for receiving the rod lenses and, following proper positioning of such lenses, the forces would be removed to permit the barrel to assume its non-circular shape for securely anchoring the rod lenses in place. It is also to be understood that temperature differences may be used in addition to, or in lieu of, such non-cylindrical variations to secure the rod lenses within the barrel. For example, heat may be applied to cause temporary expansion of the barrel until such time as the relatively cool rod lenses have been adjusted into their proper positions.

It is to be understood that the frictional mounting of the lenses are depicted in FIGS. 6–8 may be combined with adhesive attachment between the parts. Regardless of the particular mounting means selected, each succeeding rod lens of the series is precisely located in relation to a previously-mounted lens or to a master jig by means of a spacing tool 19 which is inserted into the barrel 12 (or 12') through slots 16 and which engages the corresponding (or opposing) ends of one (or both) rod lenses to insure that the lenses are correctly positioned before they are secured against relative axial movement. Therefore, referring to FIG. 5, a first rod lens 13 shown at the right is already secured in position with its end face 13a within the longitudinal limits of slots 16. A second rod lens 13, shown to the left in FIG. 5, is inserted into the tube and is urged into position by a plunger 20 or any other suitable advancing means. Advancement of the second rod lens is continued until its leading end 13a is also disposed within the longitudinal limits of the diametrically-opposed slots 16 and contacts one side of the transversely-inserted spacing tool 19. In a preferred procedure, the other side of the tool contacts the opposing end of the fixed rod lens, the tool therefore precisely spacing the opposing end faces of both lenses. Thereafter, the freshly inserted rod lens is fixed in place and the spacing tool 19 is withdrawn. The process is repeated until the full series of rod lenses has been mounted within the slotted barrel.

Slots 16 may be utilized as access ports for the introduction of a suitable adhesive for securing the rod lenses in place. It is believed apparent that a small amount of liquid adhesive, introduced through a slot 16 (or through other openings provided for that purpose) and applied to the exposed outer cylindrical surface of a rod lens along the edge of the slot, may be drawn by capillary attraction into the interior of the barrel to secure the rod lens in place. If the barrel is non-circular (e.g., oval) in cross section and the rod lenses are to be securely wholly or partially in place by clamping forces as described in connection with FIGS. 6–8, then shoes 17 and 18 would be oriented as indicated in broken lines in FIG. 5 and would engage opposite sides of the barrel to force a substantial portion of that barrel into generally cylindrical configuration during the lens inserting and adjusting steps.

After all of the lenses are secured in place and the cartridge is thereby completed, the exposed or accessible surfaces of the barrel and rod lenses may be cleaned by standard ultrasonic cleaning techniques or by any other suitable washing, rinsing, and drying procedures. Slots 16 provides access to the end faces of the lenses to insure proper cleaning of those surfaces. Such cleaning is particularly important in rod lens systems because, unlike camera systems, the faces of the lenses often lie in or near the image planes. Any particulate matter remaining upon the end face of a rod lens might therefore appear in the field of view when the completed assembly is put to use.

Upon completion of the cleaning step, the cartridge, which comprises the barrel and lenses mounted therein, may be inserted into the outer tube and secured therein. If desired, the barrel may be provided with spacing elements or rings 21 (FIG. 3) to center and help support the cartridge within the tube 11. Such rings, if used at all, would be located at two or more positions spaced a substantial distance apart along the length of the barrel, ordinarily adjacent the ends of the cartridge (or cartridges, where a plurality of such cartridges are disposed in axial relation) to insure proper optical alignment of the ends of the cartridge with other optical elements (i.e., prisms, lens groups, and other cartridges). In the illustration given, rings 21 take the form of resilient sealing elements formed of any suitable natural or synthetic elastomeric material; however, it is to be understood that such rings need not necessarily be resilient. Whether such rings are used at all depends largely on the construction of the remainder of the endoscope with which the assembly is to be used; for purposes of the present invention and the cooperative relationship of parts as described herein, such rings may be considered optional rather than essential.

FIG. 4 illustrates the floating relationship between the barrel 12 and the outer tube 11 when the assembly is flexed longitudinally. Because of the spacing 15 between the opposing surfaces of those parts, flexing of the inner tube or barrel is partially decoupled from flexing action of the outer tube. Specifically, the bending action of the barrel is localized in the region of slots 16, the slots themselves contributing to the preferential flexure in those zones. The fragile rod lenses are protected against exposure to bending forces until maximum flexure of the outer tube takes place. Further bending of the assembly tends to result in inelastic bending of the outer sheath in advance of any breakage of the rod lenses, a practical advantage because a damaged instrument is readily detected if the outer sheath is bent, whereas a fractured rod lens may not be discovered until the instrument is in use and even then it is quite possible that poor optical performance might be attributed to causes other than rod lens breakage.

FIGS. 9 and 10 depict a modified cartridge comprising a barrel or inner tube 112 containing a group of rod lenses 113a, 113b, and 113c. As shown, the lenses of the group are spaced axially apart at precise predetermined distances and are secured within the barrel by adhesive or by any other suitable means, including the clamping forces previously described through the use of a barrel of non-circular cross sectional configuration (e.g., oval or slightly triangular) in conjunction with rod lenses of cylindrical configuration. In other words, the construction and procedure shown and described in connection with FIGS. 6-8 may be utilized in fixing rod lenses 113a-113c in position within barrel 112.

Like barrel 12 provided with slots 16, barrel 112 includes slots 116, preferably of rectangular (axially elongated) configuration and arranged in groupings between the opposing end faces of adjacent lenses. Groups of three slots are illustrated and are preferred; however, each group may comprise only a pair of slots, as described in conjunction with the first embodiment, or may be composed of a number greater than three, as desired.

Each of the slots may have a length great enough to bridge the end faces of adjacent lenses, as disclosed in connection with the embodiment of FIGS. 1-5 but, in the particular form shown in FIGS. 9 and 10, each slot is of reduced length, extending in opposite axial directions beyond the end face of only a single rod lens. Thus, spacing tool 119, when inserted through a slot 116, engages the end face of only a single rod lens as shown. As long as the spacing tool is precisely positioned relative to barrel 112 as through the use of a suitable jig, each rod lens may be accurately positioned within the barrel and the spacing between opposing end faces of the lenses of the series may be precisely controlled.

After lenses 113a-113c are precisely positioned and secured within barrel 112, the accessible surfaces of the barrel and lenses are cleaned in the manner previously described. Again, slots 116 provide access to the end faces of the lenses to insure proper cleaning of those surfaces. Following cleaning, the cartridge is then inserted into an outer tube (such as tube 11 previously described) or is sealed in a suitable wrapper until insertion into such an outer tube is desired.

Each cartridge depicted in FIG. 9 contains the required number of lenses to form a relay module. A plurality of such cartridges would be disposed within an outer tube to provide the successive relay modules of a complete rod lens assembly. Thus, barrel 112 would be disposed in end-to-end relation with other similar barrels 112' in the completed assembly. As previously described, annular rings or ribs 121 may be provided to insure proper axial alignment of the successive cartridges or barrels within the outer tube 11 (not shown in FIG. 9).

As previously described, the slots contribute to preferential flexure of the barrel in those zones disposed between the ends of the rod lenses of the series. FIG. 9 illustrates in phantom lines, and somewhat exaggerated form, that the bending action of the barrel 112 is localized in the region of slots 116. The slots therefore perform the same functions in the embodiment of FIGS. 9-10 as slots 16 of the previously-described embodiment of FIGS. 1-5.

While in the foregoing, embodiments of the invention have been disclosed in considerable detail for purposes of illustration, it will be understood by those skilled in the art that many of these details may be varied without departing from the spirit and scope of the invention.

I claim:

1. A rod lens assembly comprising a flexible outer tube, an inner tube disposed within said outer tube having at least the major area of its outer surface spaced from the inner surface of said outer tube, and a series of cylindrical rod lenses disposed in longitudinal alignment within said inner tube, said lenses having their cylindrical surface portions secured to the inside surface of said inner tube and having their end faces spaced from the opposing ends of adjacent lenses of said series, and a plurality of longitudinally-spaced slots in the side wall of said inner tube, each slot being disposed between adjacent lenses in said series and extending longitudinally in both axial directions beyond at least one of the opposing end faces of a pair of said adjacent lenses.

2. The assembly of claim 1 in which each slot extends longitudinally a distance no less than the distance between the opposing end faces of the adjacent lenses.

3. The assembly of claim 1 in which said slots between successive lenses of said series are staggered at an angular distance less than 180 degrees.

4. The assembly of claim 1 in which a plurality of said slots are disposed in the side wall of said inner tube between each pair of lenses of said series.

5. The assembly of claim 4 in which said plurality constitutes a triad of uniformly-spaced slots.

6. The assembly of claim 4 in which said plurality constitutes a pair of said slots disposed in diametric opposition.

7. The assembly of claim 1 in which each slot is longer than the distance between the opposing end faces of the rod lenses adjacent thereto.

8. The assembly of claim 1 in which said inner tube is flexible and is normally of non-circular cross sectional configuration but is capable of being flexed into substantially circular configuration upon the application of lateral forces thereagainst, said inner tube when flexed into circular cross sectional configuration having an inside diameter slightly greater than the diameter of said rod lenses and when in an unflexed state having a diameter along a minor axis less than the outside diameter of said rod lenses, whereby, said lenses are clamped within said inner tube under tension of the wall thereof.

9. The assembly of claim 8 in which said flexible inner tube is oval in cross sectional configuration when said tube is in its untensioned state.

10. The assembly of claim 8 in which said inner tube is slightly triangular in configuration when the same is in its untensioned state.

11. The assembly of claim 8 in which said inner tube is formed of metal.

12. The assembly of claim 1 in which said outer tube comprises an outer flexible sheath and an inner layer having a multiplicity of light-conducting fibers.

13. The assembly of claim 12 in which said sheath is formed of metal.

14. The assembly of claim 13 in which the opposing surfaces of said inner and outer tubes are spaced apart a radial distance of approximately 20 to 40 percent of the combined radial dimension of said space and wall thickness of said sheath.

15. A method of making a rod lens assembly comprising the steps of inserting a plurality of rod lenses longitudinally into an open-ended tube having a series of longitudinally-spaced wall openings, adjusting the spacing between the opposing end faces of adjacent lenses by introducing a spacing tool transversely into said tube through each opening of said series and positioning said tool to contact at least one of the opposing end faces of said adjacent lenses to adjust the axial position thereof, and thereafter fixing said lenses in their axial positions of adjustment.

16. The method of claim 15 in which there is the further steps of cleaning the surfaces of said tube and the end faces of said rod lenses, and then mounting said tube and lenses within a protective outer tube.

17. The method of claim 16 in which said protective outer tube has an internal diameter substantially greater than the outside diameter of said first-mentioned tube.

18. The method of claim 15 in which said spacing tool is of selected width and is introduced transversely into said tube to position the same in simultaneous contact with both of said opposing end faces of said adjacent lenses.

19. The method of claim 15 in which said tube is flexible and is of non-circular cross sectional configuration with an internal dimension along a minor axis which is normally less than the outside diameter of said rod lenses but greater than the outside diameter of said lenses when the wall of said tube is flexed into generally circular cross sectional configuration, said inserting step being performed while the wall of said tube is flexed into its generally circular configuration.

20. The method of claim 19 in which said adjusting step is performed while the wall portion of said tube extending about at least one of said rod lenses is flexed into its generally circular cross sectional configuration.

21. The method of claim 20 in which said securing step includes removing the force causing said tube to assume a generally circular cross sectional configuration, thereby permitting opposite wall portions of said tube to clamp said lenses securely in their adjusted positions.

* * * * *